United States Patent [19]

Tsuda et al.

[11] Patent Number: 4,862,003
[45] Date of Patent: Aug. 29, 1989

[54] NUCLEAR MEDICAL DIAGNOSTIC APPARATUS

[75] Inventors: Kazuhiro Tsuda; Tomohiko Kihara; Kaoru Suzuki, all of Otawara, Japan

[73] Assignee: Kabushiki Kaisha Toshiba, Kawasaki, Japan

[21] Appl. No.: 135,264

[22] Filed: Dec. 21, 1987

[30] Foreign Application Priority Data

Dec. 27, 1986 [JP] Japan .............................. 61-309064

[51] Int. Cl.⁴ .............................................. G01T 1/175
[52] U.S. Cl. .................................. 250/363.02; 378/99; 378/114; 378/205
[58] Field of Search ...................... 378/99, 98, 96, 114, 378/115, 116, 62, 205; 250/363.02, 363.03, 363.04, 363.05, 363.08

[56] References Cited

U.S. PATENT DOCUMENTS 4,658,413 4/1987 Nishioka et al. ...................... 378/99

Primary Examiner—Carolyn E. Fields
Assistant Examiner—David P. Poite
Attorney, Agent, or Firm—Oblon, Spivak, McClelland, Maier & Neustadt

[57] ABSTRACT

A nuclear medical diagnostic apparatus detects and displays a radiation emitted from a local area of a body being examined after a radioisotope has been given to the body. The nuclear medical diagnostic apparatus has a function for automatically stopping the display of the detected radiation under certain conditions.

3 Claims, 3 Drawing Sheets

NUCLEAR MEDICAL DIAGNOSTIC APPARATUS

BACKGROUND OF THE INVENTION

The present invention relates to a nuclear medical diagnostic apparatus for detecting and processing, for medical diagnosis, a radiation (gamma rays) which is emitted from a radioisotope (RI) that has been given to a person being examined and selectively collected by a certain internal organ.

The conventional nuclear medical diagnostic apparatus has a relatively large and heavy radiation detector which is positioned manually by a doctor or an operator near a person (normally a patient) being examined who is laid on a bed. The radiation detector should be positioned while viewing a displayed radiation (distribution image) that is detected from the body of the person being examined. Therefore, the nuclear medical diagnostic apparatus has a display monitor located in the vicinity of the radiation detector. Since the monitor can be viewed by the operator and also the patient on the bed, hence the patient may know how the detected radiation image looks. Heretofore, the monitor is reoriented manually by the operator or the display intensity of the monitor is lowered after the radiation detector has been positioned, so that the patient cannot see the monitor image.

One problem with this practice is that the operator may forget to follow the necessary procedure. If the operator neglects the procedure, then the patient may have a chance to know the monitor image as it is detected and even the final results of the diagnosis. This may put an undesirable metal burden on the patient especially when the patient has a fatal disease.

SUMMARY OF THE INVENTION

In view of the aforesaid problem of the conventional nuclear medical diagnostic apparatus, it is an object of the present invention to provide a nuclear medical diagnostic apparatus which can reliably stop the display of a detected radiation image after a radiation detector has been positioned in place.

According to the present invention, there is provided a nuclear medical diagnostic apparatus comprising a radiation detector for detecting a radiation emitted from a body being examined, display means for displaying the detected radiation, initializing signal generating means for generating an initializing signal for updating the displayed detected radiation, and control means for generating a control signal to de-energize the display means when an interval of the initializing signal generated by the initializing signal generating means exceeds a preset time interval.

Upon elapse of the preset time interval, the display is automatically stopped, so that the diagnostic data will not be viewed by the patient.

The above and other objects, features and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
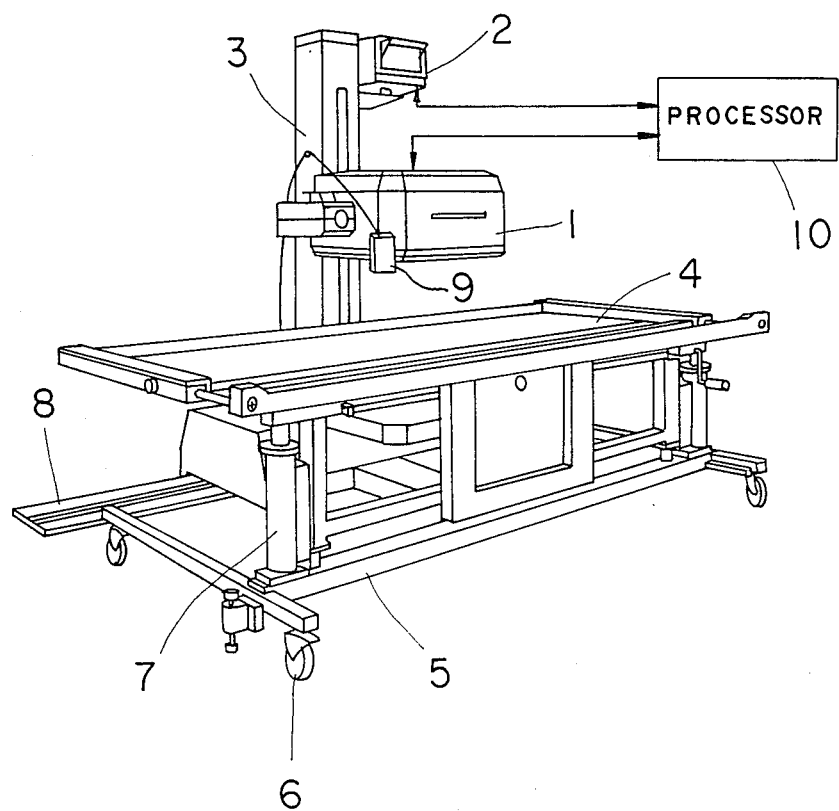
FIG. 1 is a perspective view of a perspective view of a nuclear medical diagnostic apparatus according to an embodiment of the present invention.

As shown in FIG. 1, a nuclear medical diagnostic apparatus of the present invention includes a radiation detector (gamma camera) 1 vertically movably supported on a post 3 mounted vertically on a floor. The post 3 is horizontally movable along a rail 8 on the floor. A CRT monitor or display unit 2 is mounted on an upper side portion of the post 3. A support plate 4 for placing a patient to be examined thereon is supported on a base frame 5 which is horizontally movable by casters 6. The support plate 4 is vertically movably mounted on the base frame 5 by means of a vertical shifting mechanism 7. A switch 9 is attached to the radiation detector 1 for positioning the same. A processor 10 processes data detected by the radiation detector 10 and controls the display on the display unit 2 and the like.

Figure 2:
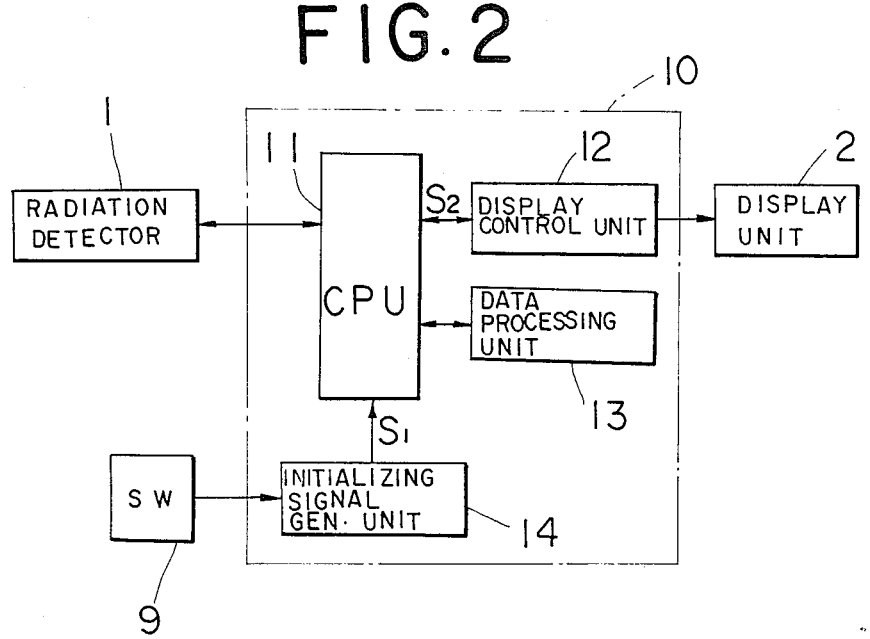
FIG. 2 is a block diagram of the nuclear medical diagnostic apparatus.

FIG. 2 shows in block form the nuclear medical diagnostic apparatus, including the details of the processor 10. The processor 10 includes a central processing unit (CPU) 11 for receiving data from the radiation detector 1, controlling operation of various components of the processor 10, and transmitting and receiving data to and from the components of the processor 10. The processor 10 also has a display control unit 12 for controlling the display on the display unit 2, a data processing unit 13 for processing data from the radiation detector 1 and generating data to be displayed, and an initializing signal generating unit 14 controlled by the positioning switch 9 for generating a pulse signal S1. When the initializing signal S1 is generated, the CPU 11 initilizes and updates the data displayed on the display unit 2 at each pulse interval of the initializing signal S1. The CPU 11 detects when the pulse interval of the signal S1 exceeds a preset time interval t, and applies a signal S2 to the display control unit 12 to de-energize the same at the time the pulse interval of the signal S1 exceeds the preset time interval t.

The preset time interval t is selected to be slightly longer than an initializing time upon positioning of the radiation detector 1.

Figure 3:
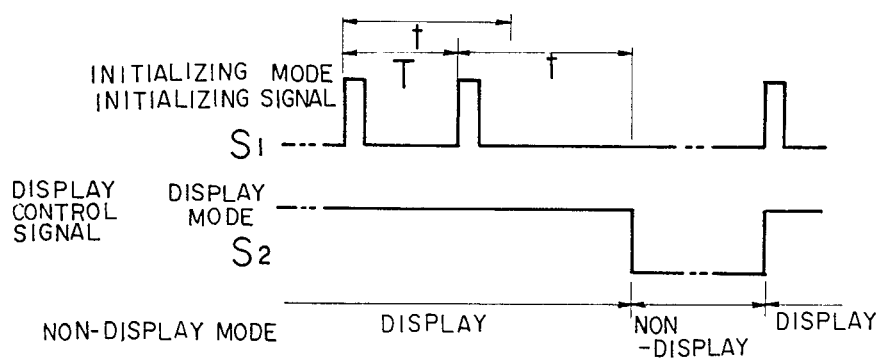
FIG. 3 is a timing chart of an operation sequence of the nuclear medical diagnostic apparatus.

Operation of the nuclear medical diagnostic apparatus thus constructed will be described below with reference to FIG. 3.

After placing a patient on the support plate 4, the operator pushes a start button (not shown) to collect data from the radiation detector 1 and energizes the display unit 2. While viewing the display on the display unit 2, the operator moves the radiation detector 1 horizontally and vertically to look for an area to be diagnosed. At this time, the positioning switch 9 is depressed. The data displayed on the display unit 2 is updated at each prescribed pulse time interval T. When the positioning of the radiation detector 1 is completed, the operator resets the positioning switch 9 in order to obtain diagnostic radiation distribution data at the detecting position. As a consequence, the signal S1 from the initializing signal generating unit 14 is stopped. The CPU 11 compares the pulse interval T of the initializing signal S1 with the preset time interval t. Since the initializing signal S1 is not produced in excess of the preset time interval t, the CPU 11 applies the signal S2 to the display control unit 12 to de-energize the same. Thus, a display mode and a non-display mode are produced as shown in FIG. 3.

When positioning the radiation detector 1 again, the positioning switch 9 is pushed to generate the initializing signal S1. The CPU 11 compares the pulse time interval T of the initializing signal S1 with the preset time interval t for the control of the display on the display unit 2.

Since the display on the display unit 2 is automatically stopped if the pulse interval T of the initializing signal S1 exceeds the preset time interval t, as described above, the detected radiation data is prevented from being continuously displayed on the display unit 2 after the radiation detector 1 has been positioned. Inasmuch as the display unit 2 is thus reliably de-energized after the radiation detector 1 has been positioned, the diagnostic data will not be viewed by the patient being examined, and a mental burden placed on the patient can be reduced.

Figure 4:
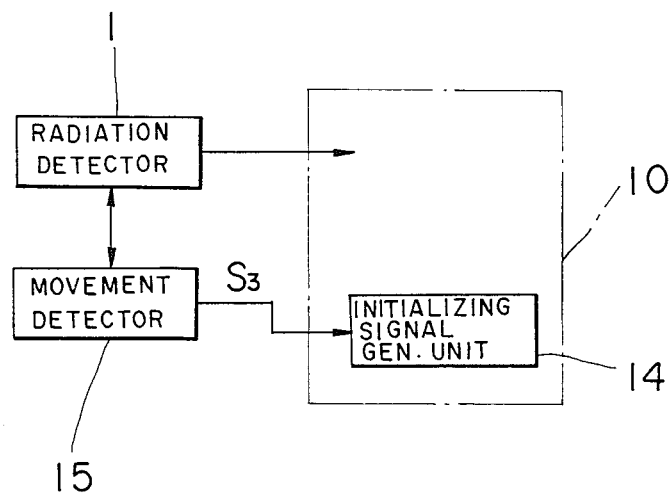
FIG. 4 is a block diagram of a perspective view of a nuclear medical diagnostic apparatus according to another embodiment of the present invention.

FIG. 4 shows a nuclear medical diagnostic apparatus according to another embodiment of the present invention. The nuclear medical diagnostic apparatus shown in FIG. 4 includes, rather than the positioning switch 9 of FIG. 2, a movement detector 15 for detecting whether the radiation detector 1 is moved or not. While the radiation detector 1 is being moved so that it will be positioned in place, the initializing signal generating unit 14 is operated. When the movement of the radiation detector 1 is stopped, the movement detector 15 generates a control signal S3 for stopping the operation of the initializing signal generating unit 14. With this arrangement, the operator is not required to operate any positioning switch.

Although certain preferred embodiments have been shown and described, it should be understood that many changes and modifications may be made therein without departing from the scope of the appended claims.

What is claimed is:

1. A nuclear medical diagnostic apparatus comprising:
    a gamma ray detector for detecting gamma rays emitted from a body being examined in reference to a radioisotope applied to the body;
    display means arranged near the gamma ray detector so as to display a result of detection of the gamma rays;
    an initializing signal generating means for generating a periodic initializing signal to update the display of the result of detection of said gamma rays; and
    a control means for comparing the period of the initializing signal with a predetermined setting time and generating a signal for stopping the display of said display means when said comparing indicates that the period of the initializing signal exceeds said predetermined time.

2. A nuclear medical diagnostic apparatus according to claim 1, comprising:
    an operation switch arranged at said gamma ray detector, wherein control of said initializing signal generating means is carried out by means of said operation switch to result in stopping of the display.

3. A nuclear medical diagnostic apparatus according to claim 1, comprising:
    movement detection means for detecting a moving condition of said gamma ray detector, wherein control of said initializing signal generating means is carried out with an output from said movement detection means to result in stopping of the display.

* * * * *

UNITED STATES PATENT AND TRADEMARK OFFICE
CERTIFICATE OF CORRECTION

PATENT NO. : 4,862,003

DATED : August 29, 1989

INVENTOR(S) : Kazuhiro Tsuda et al.

It is certified that error appears in the above-identified patent and that said Letters Patent is hereby corrected as shown below:

Column 1, line 34, change "metal" to --mental--.

Signed and Sealed this

Ninth Day of October, 1990

Attest:

HARRY F. MANBECK, JR.

Attesting Officer

Commissioner of Patents and Trademarks